(12) United States Patent
Mertens

(10) Patent No.: US 7,067,095 B1
(45) Date of Patent: Jun. 27, 2006

(54) SYNTHESIS OF SILICOALUMINOPHOSPHATE MOLECULAR SIEVES

(75) Inventor: Machteld Maria Mertens, Boortmeerbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/059,945

(22) Filed: Feb. 17, 2005

Related U.S. Application Data

(60) Provisional application No. 60/634,655, filed on Dec. 9, 2004.

(51) Int. Cl.
*C01B 37/08* (2006.01)

(52) U.S. Cl. .............................. 423/306; 423/DIG. 30; 502/214

(58) Field of Classification Search ................ 423/305, 423/306, DIG. 30; 502/208, 214; 585/640
See application file for complete search history.

(56) References Cited

U.S. PATENT DOCUMENTS

| 4,440,871 A | 4/1984 | Lok et al. .................... 502/214 |
| 5,279,810 A | 1/1994 | Calabro ....................... 423/701 |
| 6,334,994 B1 | 1/2002 | Wendelbo et al. .......... 423/718 |
| 2002/0165089 A1* | 11/2002 | Janssen et al. ............... 502/214 |
| 2002/0165090 A1* | 11/2002 | Janssen et al. ............... 502/214 |

FOREIGN PATENT DOCUMENTS

| WO | WO 02/70407 | 9/2002 |
| WO | WO 2003040037 A1 * | 5/2003 |

OTHER PUBLICATIONS

J. Chen et al, "Understanding the Bronsted Acidity of SAPO-5, SAPO-17, SAPO-18 and SAPO-34 and their Catalytic Performance for Methanol Conversion to Hydrocarbons", Studies in Surface Science and Catalysis, vol. 84, pp. 1731-1738.

J. Chen et al, "SAPO-18 Catalysts and Their Bronsted Acid Sites", Journal of Physical Chemistry, vol. 98, pp. 10216-10224 (1994).

J. Chen et al, "Silicoaluminophosphate Number Eighteen (SAPO-18): A New Microporous Solid Acid Catalyst", Catalysis Letters, vol. 28, pp. 241-248 (1994).

A.M. Prakash et al, "Synthesis of SAPO-34: High Silicon Incorporation in the Presence of Morpholine as Template", Journal of the Chemical Society, Faraday Transactions, vol. 90(15), pp. 2291-2296 (1994).

Yan Xu et al, "The Synthesis of SAPO-34 and CoSAPO-34 from a Triethylamine-Hydrofluroic Acid—Water System", Journal of Chemical Society, Faraday Transactions, vol. 86(2), pp. 425-429 (1990).

O.B. Vistad, et al, "Identification of a Key Precursor Phase for Synthesis of SAPO-34 and Kinetics of Formation Investigated by In Situ X-Ray Diffraction" J. Phys. Chem. B, 2001, 105, pp. 12437-12447 (2001).

N.J. Tapp et al, "Synthesis of $AlPO_4$-11", Zeolites, May 1988, vol. 18, pp. 183-188.

M.M.J. Tracey et al, "A General Recursion Method for Calculating Diffracted Intensities from Crystals Containing Planar Faults", Proceedings of the Royal Chemical Society, London, A (1991), vol. 433, pp. 499-520.

* cited by examiner

*Primary Examiner*—David Sample

(57) ABSTRACT

In a method of synthesizing a silicoaluminophosphate molecular sieve comprising at least one intergrown phase of an AEI framework type material and a CHA framework type material, a first synthesis mixture is prepared comprising water and sources of phosphorus, aluminum and optionally silicon. The first synthesis mixture is then heated under agitation to a first temperature to form an intermediate product mixture containing a silicoaluminophosphate or aluminophosphate precursor material. The intermediate product mixture is then cooled and stored at a second temperature lower than the first temperature, whereafter a second synthesis mixture is prepared comprising at least part of the intermediate product mixture and at least one organic directing agent. The second synthesis mixture is heated to a third temperature higher than the second temperature to convert at least part of the precursor material into the desired molecular sieve and the molecular sieve is recovered.

36 Claims, 2 Drawing Sheets

US 7,067,095 B1

SYNTHESIS OF SILICOALUMINOPHOSPHATE MOLECULAR SIEVES

CROSS REFERENCE TO RELATED APPLICATIONS

This application claims the benefit of Provisional Application No. 60/634,655 filed Dec. 9, 2004, the disclosure of which is fully incorporated herein by reference.

FIELD OF INVENTION

This invention relates to the synthesis of silicoaluminophosphate molecular sieves and to the use of the resultant molecular sieves in the conversion of oxygenates, particularly methanol, to olefins, particularly ethylene and propylene.

BACKGROUND OF INVENTION

Light olefins, such as ethylene, propylene, butylenes and mixtures thereof, serve as feeds for the production of numerous important chemicals and polymers. Typically, $C_2$–$C_4$ light olefins are produced by cracking petroleum refinery streams, such as $C_3$+ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$–$C_4$ alkanols, especially methanol and ethanol; $C_2$–$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Crystalline molecular sieves have a 3-dimensional, four-connected framework structure of corner-sharing [$TO_4$] tetrahedra, where T is any tetrahedrally coordinated cation. Among the known forms of molecular sieve are aluminosilicates, which contain a three-dimensional microporous crystal framework structure of [$SiO_4$] and [$AlO_4$] corner sharing tetrahedral units silicoaluminophosphates (SAPOs), in which the framework structure is composed of [$SiO_4$], [$AlO_4$] and [$PO_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Among the molecular sieves that have been investigated for use as oxygenate conversion catalysts, materials having the framework type of the zeolitic mineral chabazite (CHA) have shown particular promise. For example, SAPO-34 is a crystalline silicoaluminophosphate molecular sieve of the CHA framework type and has been found to exhibit relatively high product selectivity to ethylene and propylene, and low product selectivity to paraffins and olefins with four or more carbon atoms.

The preparation and characterization of SAPO-34 have been reported in several publications, including U.S. Pat. No. 4,440,871; J. Chen et al. in "Studies in Surface Science and Catalysis", Vol. 84, pp. 1731–1738; U.S. Pat. No. 5,279,810; J. Chen et al. in "Journal of Physical Chemistry", Vol. 98, pp. 10216–10224 (1994); J. Chen et al. in "Catalysis Letters", Vol. 28, pp. 241–248 (1994); A. M. Prakash et al. in "Journal of the Chemical Society, Faraday Transactions" Vol. 90(15), pp. 2291–2296 (1994); Yan Xu et al. in "Journal of the Chemical Society, Faraday Transactions" Vol. 86(2), pp. 425–429 (1990).

According to the article entitled "Identification of a Key Precursor Phase for Synthesis of SAPO-34 and Kinetics of Formation Investigated by In Situ X-ray Diffraction" by O. B. Vistad et al., J. Phys. Chem. B, 2001, 105, pages 12437–12447, the synthesis of SAPO-34 in the presence of HF and with morpholine as a structure directing agent proceeds through the formation of a layered crystalline precursor phase. The layered precursor is reported to be formed at synthesis temperatures of 90° C. to 150° C., whereas SAPO-34 is formed at temperatures of 170° C. to 210° C.

Similarly, the article entitled "Synthesis of $AlPO_4$-11" by N. J. Tapp et al., Zeolites, 1988, Vol. 8, 183–188 discloses that the synthesis of $AlPO_4$-11 free of condensed phase impurities is aided by pretreatment of the synthesis gel at 90° C. The pretreatment is reported to produce a poorly crystalline metavariscite/variscite phase that is transformed to $AlPO_4$-11 on raising the temperature to 200° C.

Regular crystalline molecular sieves, such as the CHA framework type materials, are built from structurally invariant building units, called Periodic Building Units, and are periodically ordered in three dimensions. Disordered structures showing periodic ordering in less than three dimensions are, however, also known. One such disordered structure is a disordered planar intergrowth in which the building units from more than one framework type, e.g., both AEI and CHA, are present. One well-known method for characterizing crystalline materials with planar faults is DIFFaX, a computer program based on a mathematical model for calculating intensities from crystals containing planar faults (see M. M. J. Tracey et al., Proceedings of the Royal Chemical Society, London, A [1991], Vol. 433, pp. 499–520).

International Patent Publication No. WO 02/70407, published Sep. 12, 2002 and incorporated herein by reference, discloses a silicoaluminophosphate molecular sieve, now designated EMM-2, comprising at least one intergrown form of molecular sieves having AEI and CHA framework types, wherein said intergrown form has an AEI/CHA ratio of from about 5/95 to 40/60 as determined by DIFFaX analysis, using the powder X-ray diffraction pattern of a calcined sample of said silicoaluminophosphate molecular sieve. EMM-2 has been found to exhibit significant activity and selectivity as a catalyst for the production of light olefins from methanol (MTO).

According to International Patent Publication No. WO 02/70407, EMM-2 can be synthesized by mixing reactive sources of silicon, phosphorus and a hydrated aluminum oxide in the presence of an organic directing agent, particularly a tetraethylammonium compound. The resultant mixture is stirred and heated to a crystallization temperature, preferably from 150° C. to 185° C., and then maintained at this temperature under stirring for between 2 and 150 hours.

U.S. Pat. No. 6,334,994, incorporated herein by reference, discloses a silicoaluminophosphate molecular sieve, referred to as RUW-19, which is also said to be an AEI/CHA mixed phase composition. In particular, RUW-19 is reported as having peaks characteristic of both AEI and CHA framework type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. DIFFaX analysis of the X-ray diffraction pattern of RUW-19 as produced in Examples 1, 2 and 3 of U.S. Pat. No. 6,334,994 indicates that these materials are characterized by single intergrown forms of AEI and CHA framework type molecular sieves with AEI/CHA ratios of about 60/40, 65/35 and 70/30.

According to the '994 patent, RUW-19 can be synthesized by initially mixing an Al-source, particularly Al-isopropoxide, with water and a P-source, particularly phosphoric acid, and thereafter adding a Si-source, particularly colloidal silica and an organic template material, particularly tetraethylammonium hydroxide, to produce a precursor gel. The gel is then put into a steel autoclave and, after an aging period at room temperature, the autoclave is heated to a maximum temperature between 180° C. and 260° C., preferably at least 200° C., for at least 1 hour, with the autoclave being shaken, stirred or rotated during the entire process of aging and crystallization. Factors which are said to enhance the production of the mixed phase RUW-19 material include maintaining the $SiO_2$ content of the gel below 5%, reducing the liquid content of the gel after addition of the $SiO_2$ source and crystallization at temperatures of 250° C. to 260° C. Pure AEI and CHA phases are said to be favored at temperatures of 200° C. to 230° C.

Study of the synthesis of EMM-2 has now shown that the crystallization process to produce such AEI/CHA intergrowths proceeds through the formation of a (silico)aluminophosphate hydrate precursor, such as ALPO-H3 and/or variscite and/or metavariscite, during heat-up of the mixture, followed by dissolution of the precursor as the intergrown molecular sieve nucleates. Moreover, it has been found that optimal conditions for the formation of the precursor are different from the optimal conditions for conversion of the precursor to the intergrown molecular sieve. For example, whereas agitation of the synthesis mixture seems to be important in initial precursor formation, synthesis of the intergrown molecular sieve from the precursor slurry can proceed with no or reduced agitation. In addition, the presence of an organic directing agent seems to be more important during nucleation of EMM-2 than during precursor formation. In fact, the absence of an organic directing agent seems to allow the precursor to crystallize under more mild conditions (for example at lower temperature).

Accordingly, the present invention provides a method of synthesizing a silicoaluminophosphate molecular sieve comprising at least one intergrown phase of an AEI framework type and a CHA framework type, in which the precursor formation stage and the molecular sieve nucleation stage are decoupled whereby each stage can be conducted under the most advantageous conditions.

SUMMARY

In one aspect, the invention resides in a method of synthesizing a silicoaluminophosphate molecular sieve comprising at least one intergrown phase of an AEI framework type material and a CHA framework type material, the method comprising:

(a) preparing a first synthesis mixture comprising water and sources of phosphorus, aluminum and optionally silicon;

(b) heating said first synthesis mixture under agitation to a first temperature to form an intermediate product mixture containing a silicoaluminophosphate or aluminophosphate precursor material; and (c) cooling and storing the intermediate product mixture at a second temperature lower than said first temperature;

(d) preparing a second synthesis mixture comprising at least part of said intermediate product mixture from (c) and at least one organic directing agent;

(e) heating said second synthesis mixture to a third temperature higher than said first temperature to convert at least part of said precursor material into said molecular sieve; and (f) recovering said molecular sieve.

Conveniently, said first temperature is from about 99° C. to about 150° C., such as about 115° C. to about 125° C.

Conveniently, said second temperature is less than 50° C., such as from about 0° C. to about 30° C.

Conveniently, said third temperature is higher than said first temperature, for example from about 150° C. to about 220° C., such as from about 165° C. to about 190° C.

Conveniently, the pH of the first synthesis mixture is less than 2, such as between about 1.1 and about 1.5. Conveniently, the pH of the second synthesis mixture is between about 5 and about 12, such as between about 6 and about 8.

Conveniently, the $P_2O_5:Al_2O_3$ of the first synthesis mixture is between about 0.7 and about 1.0, such as between about 0.75 and about 0.9.

In one embodiment, the first synthesis mixture also comprises said at least one organic directing agent (R), in which case the second synthesis mixture conveniently has the same composition as the intermediate product mixture. Typically, however, the $R:Al_2O_3$ molar ratio of the second synthesis mixture is greater than that of the first synthesis mixture. Conveniently, the $R:Al_2O_3$ molar ratio of the second synthesis mixture is greater than 0.6, such as about 0.65 to about 1, and the $R:Al_2O_3$ molar ratio of the first synthesis mixture is less than 0.7, such as about 0.2 to about 0.6.

Conveniently, the $H_2O:Al_2O_3$ molar ratio of the first synthesis mixture is at least 30, such as about 30 to about 50.

Conveniently, the method also comprises reducing the water content of the intermediate product mixture prior to storage thereof. In such a case, preparing the second synthesis mixture in (d) conveniently also comprises adding water to said intermediate product mixture from (c). In one embodiment, the $H_2O:Al_2O_3$ molar ratio of the second synthesis mixture is the same as that of the first synthesis mixture.

Conveniently, said precursor material comprises at least one of ALPO-H3, variscite and metavariscite.

Conveniently, the heating in (b) is conducted so as to raise the temperature of said first synthesis mixture at a rate of at least 8° C./hour, such as at a rate of from about 10° C./hour to about 40° C./hour. Conveniently, the heating in (e) is also conducted so as to raise the temperature of said second synthesis mixture at a rate of at least 8° C./hour, such as at a rate of from about 10° C./hour to about 40° C./hour. In one embodiment, the heating (e) is conducted without agitation.

Conveniently, (c) comprises storing said cooled intermediate product mixture for at least 2 hours, such as for about 30 hours to about 30 days, before the heating (e).

In one embodiment, said at least one intergrown phase has an AEI/CHA ratio of from about 5/95 to about 40/60, for example from about 10/90 to about 30/70, such as from about 15/85 to about 20/80, as determined by DIFFaX analysis. In a further embodiment, the silicoaluminophosphate molecular sieve comprises first and second intergrown phases each of an AEI framework type material and a CHA framework type material, the first intergrown phase having an AEI/CHA ratio of from about 5/95 to about 40/60 as determined by DIFFaX analysis, and the second intergrown phase having a different AEI/CHA ratio from said first intergrown form, such as an AEI/CHA ratio of about 50/50 as determined by DIFFaX analysis.

In further aspects, the invention resides in a silicoaluminophosphate molecular sieve produced by the method described herein and to use of the molecular sieve in a process for converting an oxygenate-containing feedstock to a product comprising olefins.

DETAILED DESCRIPTION OF THE EMBODIMENTS

Figure 1A:
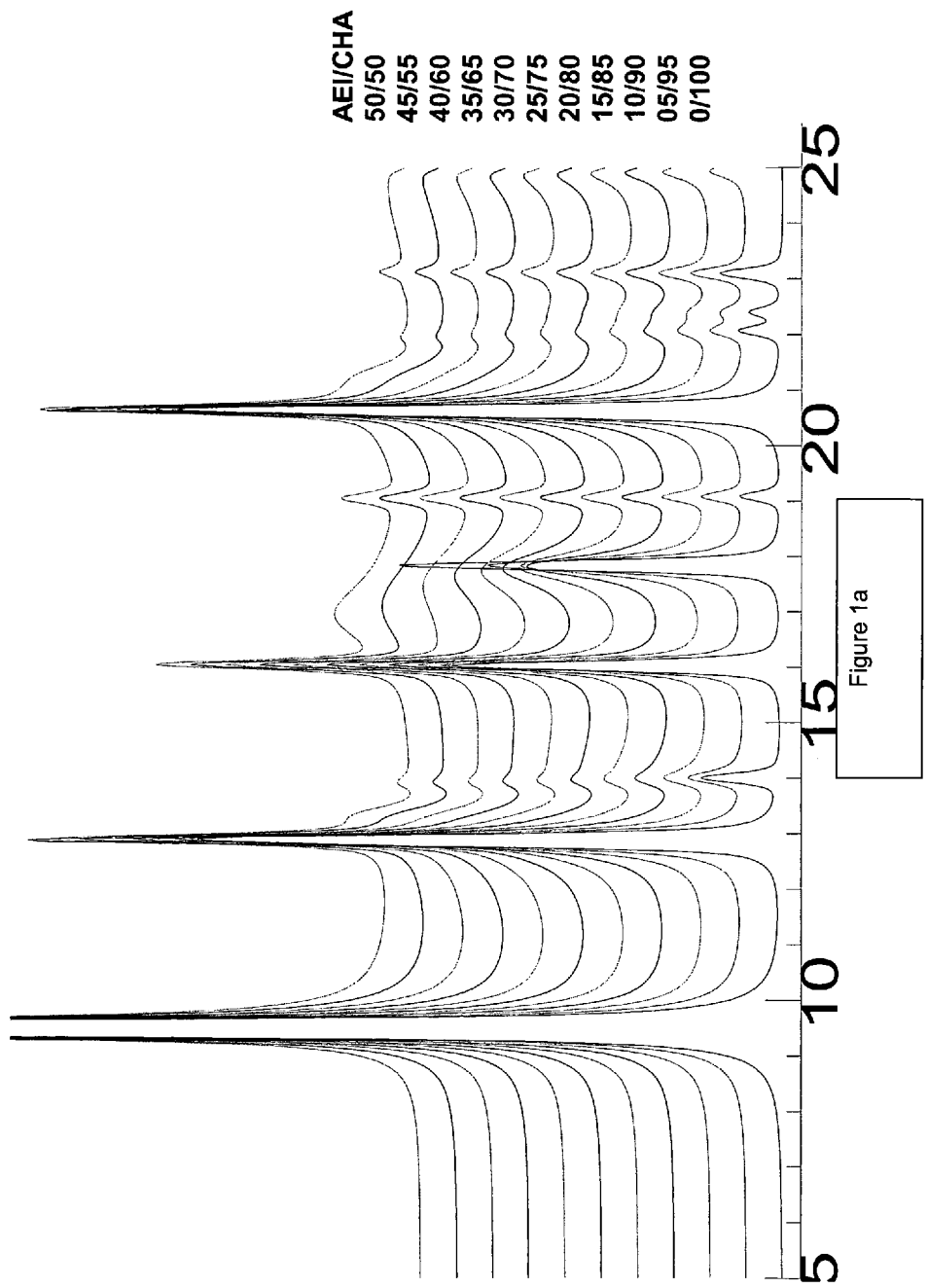
FIGS. 1a and 1b are DIFFaX simulated diffraction patterns for intergrown AEI/CHA phases having varying AEI/CHA ratios.

The present invention relates to the synthesis of a crystalline silicoaluminophosphate molecular sieve comprising at least one intergrown form of an AEI framework type material and a CHA framework type material, and to the use of the resultant molecular sieve in the conversion of oxygenates, particularly methanol, to olefins, particularly ethylene and propylene.

According to the invention, it has been found that the synthesis of AEI/CHA intergrowths proceeds through the formation, and subsequent dissolution, of certain (silico) aluminophosphate hydrate precursors, such as ALPO-H3, variscite and/or metavariscite. Moreover, it has been found that the optimal conditions for precursor formation are different from those for precursor dissolution/molecular sieve nucleation. The synthesis method of the invention therefore seeks to decouple the initial formation of the precursor from the subsequent dissolution of the precursor and nucleation of the intergrown molecular sieve. In this way, it is possible to independently optimize the conditions employed in each stage of the synthesis.

Molecular Sieve

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

The intergrown silicoaluminophosphate molecular sieves described herein are disordered planar intergrowth of end-member structures AEI and CHA. For AEI and CHA structure types, the Periodic Building Unit is a double six ring layer. There are two types of layers "a" and "b", which are topologically identical except "b" is the mirror image of "a". When layers of the same type stack on top of one another, i.e. . . . aaa . . . or . . . bbb . . . , the framework type CHA is generated. When layers "a" and "b" alternate, e.g., . . . abab . . . , a different framework type, namely AEI, is generated. The intergrown molecular sieves described herein comprise stackings of layers "a" and "b" containing regions of CHA framework type and regions of AEI framework type. Each change of CHA to AEI framework type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499–520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543–550.

Figure 1B:
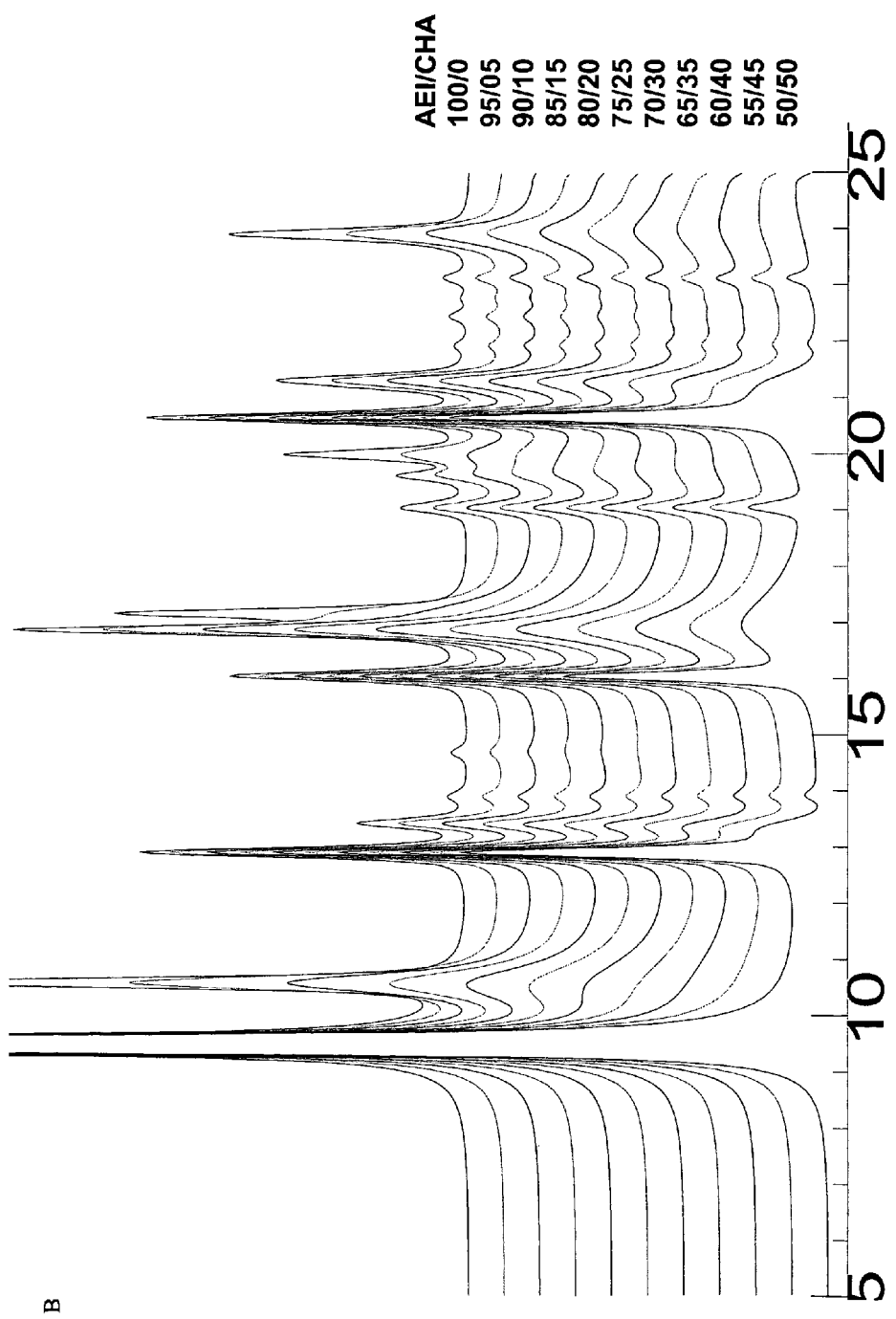

FIGS. 1a and 1b show the simulated diffraction patterns obtained for intergrowths of a CHA framework type molecular sieve with an AEI framework type molecular sieve having various AEI/CHA ratios. FIG. 1a shows the diffraction patterns in the 15 to 35 (2θ) range simulated by DIFFaX for intergrown phases with AEI/CHA ratios of 0/100 (CHA end-member), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50). FIG. 1b shows the diffraction patterns in the range of 5 to 20 (2θ) simulated by DIFFaX for intergrown phases with AEI/CHA ratios of 0/100 (CHA end-member), 10/90 (AEI/CHA=0.11), 20/80 (AEI/CHA=0,25), 50/50 (AEI/CHA=1,0), 70/30 (AEI/CHA=2.33), 80/20 (AEI/CHA=4.0), 100/0 (AEI end-member). All XRD diffraction patterns are normalized to the highest peak of the entire set of simulated patterns, i.e. the peak at about 9.5 degrees 2θ for pure CHA (AEI/CHA ratio of 0/100). Such normalization of intensity values allows a quantitative determination of mixtures of intergrowths As the ratio of AEI increases relative to CHA in the intergrown phase, one can observe a decrease in intensity of certain peaks, for example, the peak at about 2θ=25.0 and an increase in intensity of other peaks, for example the peak at about 2θ=17.05 and the shoulder at 2θ=21.2. Intergrown phases with AEI/CHA ratios of 50/50 and above (AEI/CHA≧1.0) show a broad feature centered at about 16.9 (2θ).

In a preferred embodiment, the intergrown silicoaluminophosphate molecular sieve employed in the catalyst composition of the invention is at least one intergrowth of an AEI framework type and a CHA framework type, wherein said at least one intergrowth has an AEI/CHA ratio of from about 5/95 to about 40/60, for example from about 10/90 to about 30/70, such as from about 15/85 to about 20/80, as determined by DIFFaX analysis. Such a CHA-rich intergrowth is characterized by a powder XRD diffraction pattern (obtained from a sample after calcination and without rehydration after calcination) having at least the reflections in the 5 to 25 (2θ) range as shown in Table 1 below:

TABLE 1

| 2θ (CuKα) |
| --- |
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0 |

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not extra-framework material such as water or template in the cavities. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. Recording under the same conditions immediately after removal of the Mylar foil will also provide a diffraction pattern suitable for use in DIFFaX analysis.

In an alternative embodiment, the intergrown silicoaluminophosphate molecular sieve produced by the synthesis method of the invention comprises a plurality of intergrown forms of the CHA and AEI framework types, typically with a first intergrown form having an AEI/CHA ratio of from about 5/95 to about 40/60, as determined by DIFFaX analysis, and a second intergrown form having a different AEI/CHA ratio from said first intergrown form. The second intergrown form typically has an AEI/CHA ratio of about 30/70 to about 55/45, such as about 50/50, as determined by DIFFaX analysis, in which case the XRD diffraction pattern exhibits a broad feature centered at about 16.9 (2θ) in addition to the reflection peaks listed in Table 1.

Preferably, the CHA framework type molecular sieve in the intergrowth of the invention is SAPO-34 and the AEI framework type molecular sieve is selected from SAPO-18, ALPO-18 and mixtures thereof. In addition, the intergrown silicoaluminophosphate preferably has a framework silica to alumina molar ratio ($Si/Al_2$) greater than 0.16 and less than 0.19, such as from about 0.165 to about 0.185, for example about 0.18. The framework silica to alumina molar ratio is conveniently determined by NMR analysis.

Molecular Sieve Synthesis

The molecular sieve synthesis method of the invention comprises three stages; namely a first stage in which a silicoaluminophosphate or aluminophosphate precursor material is produced, a second storage stage, and a third stage in which the precursor material is converted into the desired intergrown AEI/CHA framework type molecular sieve.

In the first synthesis stage, water is initially combined with reactive sources of phosphorus, aluminum and optionally silicon, to form a first synthesis mixture having a molar composition within the following ranges:

$P_2O_5:Al_2O_3$=about 0.7 to about 1.0, such as about 0.75 to about 0.9;

$H_2O:Al_2O_3$=at least 30, such as from about 30 to about 50; and $SiO_2:Al_2O_3$=0 to about 0.3, such as about 0.1 to about 0.2.

In addition, an organic structure directing agent (R) can be incorporated in the first synthesis mixture, in which case the $R:Al_2O_3$ ratio of the first synthesis mixture is typically below 0.7, such as from about 0.2 to about 0.6.

The reactive source of phosphorus used in the first synthesis mixture is conveniently phosphoric acid. Examples of suitable reactive aluminum sources include hydrated aluminum oxides such as boehmite and pseudoboehmite. Preferably, pseudoboehmite is used. Where present, the reactive source of silicon may be a silicate, e.g., fumed silica, such as Aerosil (available from Degussa), a tetraalkyl orthosilicate, or an aqueous colloidal suspension of silica, for example that sold by E.I. du Pont de Nemours under the tradename Ludox. The organic structure directing agent conveniently includes a tetraethyl ammonium compound, such as tetraethyl ammonium hydroxide (TEAOH), tetraethyl ammonium phosphate, tetraethyl ammonium fluoride, tetraethyl ammonium bromide, tetraethyl ammonium chloride or tetraethyl ammonium acetate. Typically, the directing agent includes tetraethyl ammonium hydroxide. In some cases, more than one organic structure directing agent may be employed, such as a combination of a tetraethyl ammonium compound and dipropylamine.

The pH of the first synthesis mixture is preferably arranged to be less than 2, such as between about 1.1 and about 1.5, and can, if necessary, be adjusted to be within the desired range by addition of acid or base to the first synthesis mixture.

The first synthesis mixture is then heated so as to raise its temperature at a rate of at least 8° C./hour, such as at a rate of from about 10° C./hour to about 40° C./hour, to a first temperature of about 99° C. to about 150° C., such as about 115° C. to about 125° C. During heating, the first synthesis mixture is continuously agitated (i.e. by mixing, stirring, tumbling, shaking, swinging or any other mode of agitation) with an intensity that avoids precipitation of the mixture components. The first synthesis mixture is then maintained at said first temperature, preferably with the agitation being continued, for a time, typically from about 0.5 hours to about 120 hours, to form an intermediate product mixture containing a slurry of a silicoaluminophosphate or aluminophosphate precursor material. The precursor material is different from the final intergrown AEI/CHA framework type molecular sieve and generally comprises at least one of ALPO-H3, variscite and metavariscite.

After precursor formation, the intermediate product mixture is cooled from the first temperature to a second, lower temperature, typically less than 50° C., such as from about 0° C. to about 30° C., and is then stored at this lower temperature until it is desired to produce the final intergrown molecular sieve. Typically, the storage time is at least 2 hours, such as from about 30 hours to about 30 days. In addition, prior to storage, it may be desirable to at least partially dry the precursor slurry to reduce its $H_2O:Al_2O_3$ ratio.

Following storage, additional water can be added to the precursor material, especially where the precursor slurry is dried before storage, optionally together with a reactive silica source or additional reactive silica source and an organic directing agent or additional organic directing agent to produce a second synthesis mixture having a molar composition within the following ranges:

$P_2O_5:Al_2O_3$=about 0.7 to about 1.0, such as about 0.75 to about 0.9;

$H_2O:Al_2O_3$=at least 30, such as from about 30 to about 50;

$SiO_2:Al_2O_3$=about 0.05 to about 0.3, such as about 0.1 to about 0.2; and $R:Al_2O_3$=at least 0.6, such as about 0.65 to about 1.0.

It is, however, to be appreciated that, where an organic directing agent is present in the first synthesis mixture, the intermediate product mixture can be used as-is to produce the desired AEI/CHA intergrowth. In other words, the second synthesis mixture can have the same composition as the intermediate product mixture.

The pH of the second synthesis mixture is generally not critical, but typically is arranged to between about 5 and about 12, such as between about 6 and about 8.

The second synthesis mixture is then heated so as to raise its temperature at a rate of at least 8° C./hour, such as at a rate of from about 10° C./hour to about 40° C./hour, to a third temperature higher than the first temperature and generally from about 150° C. to about 220° C., such as about 165° C. to about 190° C. This second heating step can be conducted under static conditions or with reduced agitation as compared with the first heating step. The second synthesis mixture is then maintained at said third temperature until the intergrown molecular sieve crystallizes from the mixture, which generally takes from 2 to 150 hours; such as from about 5 to about 100 hours, for example from about 10 to about 50 hours.

The crystalline product can then be recovered by any standard means, such as by centrifugation or filtration. The separated product can also be washed, recovered by centrifugation or filtration and dried. The crystalline product is typically in the form of plates, platelets, stacked platelets or cubes. Typically the crystals have a $d_{50}$ (50% by volume of crystals is smaller than the $d_{50}$ value) particle size from about 0.1 to about 3 μm, such as about 0.5 to about 2.0 μm, for example about 1.3 to about 1.9 μm.

Synthesis of the desired AEI/CHA intergrowth may be facilitated by the presence of at least 0.1 ppm, such as at least 10 ppm, for example at least 100 ppm, conveniently at least 500 ppm of seed crystals based on total weight of the reaction mixture. The seed crystals can be homostructural with the crystalline material of the present invention, for example the product of a previous synthesis, or can be a heterostructural crystalline material, such as an AEI, LEV, CHA or ERI structure-type molecular sieve. The seed crystals can have the same composition as, or can have a different composition (e.g., the seeds can be an aluminosilicate) from, the crystalline material of the present invention. The seeds can be added to the first synthesis mixture, the second synthesis mixture or to both mixtures.

The crystalline product recovered from the second synthesis mixture contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system.

Molecular Sieve Catalyst Compositions

The intergrown molecular sieve produced by the synthesis method of the invention can be used in a wide variety of catalytic and non-catalytic applications, but is particularly intended for use as a catalyst in the conversion of oxygenates to olefins. Before use in such a process, the intergrown molecular sieve will normally be formulated into a catalyst composition by combination with other materials, such as binders and/or matrix materials, which provide additional hardness or catalytic activity to the finished catalyst.

Materials which can be blended with the intergrown crystalline material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product ranges from 10 to 90 weight percent of the total catalyst, preferably 20 to 80 weight percent of the total catalyst.

Use of the Molecular Sieve

The silicoaluminophosphate molecular sieves produced by the method of the invention are useful as catalysts in a variety of processes including cracking of, for example, a naphtha feed to light olefin(s) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins;

transalkylation of, for example, a combination of aromatic and polyalkylaromatic hydrocarbons; dealkylation; dehydrocyclization; disproportionation of, for example, toluene to make benzene and paraxylene; oligomerization of, for example, straight and branched chain olefin(s); and the synthesis of monoalkylamines and dialkylamines.

In particular, the intergrown molecular sieves described herein are useful in the catalytic conversion of oxygenates to olefins. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is (are) generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

Using the various oxygenate feedstocks discussed above, particularly a feedstock containing methanol, the catalyst composition of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The resultant olefins can be separated from the oxygenate conversion product for sale or can be fed to a downstream process for converting the olefins to, for example, polymers.

The invention will now be more particularly described with reference to the following Example.

In the Example, DIFFaX analysis was used to determine the AEI/CHA ratio of the molecular sieves. Simulated powder XRD diffraction patterns for varying ratios of AEI/CHA were generated using the DIFFaX program available from the International Zeolite Association (see also M. M. J. Tracey et al., Proceedings of the Royal Chemical Society, London, A (1991), Vol. 433, pp. 499–520 "Collection of Simulated XRD Powder Patterns for Zeolites" by M. M. J. Treacy and J. B. Higgins, 2001, Fourth Edition, published on behalf of the Structure Commission of the International Zeolite Association). The DIFFaX input file used to simulate the XRD diffraction patterns is given in Table 2 of U.S. Patent Application Publication No. 2002/0165089, incorporated herein by reference. In order to obtain best fitting between the DIFFaX simulated patterns and the experimental patterns, two sets of simulated XRD patterns were generated using a line broadening of 0.009 (as described in U.S. Patent Application No. 2002/0165089) and a line broadening of 0.04 (FIGS. 1a and 1b). The simulated diffraction patterns were then compared with the experimental powder XRD diffraction patterns. In this respect, a very sensitive range is the 15 to 19.5 2θ range.

EXAMPLE 1

A mixture of 381.81 g of phosphoric acid (85% in water, Acros), 371.88 g of demineralized water and 25.64 g Ludox AS 40 (40% silica) was prepared. To this mixture 695.85 g of a tetraethylammonium hydroxide solution (35% in water) was added. To the resultant mixture was added 224.86 g of alumina (Condea Pural SB-1). A slurry was produced and was transferred to a 2 liter Parr stainless steel autoclave. The composition of the mixture in terms of molar ratios was as follows:

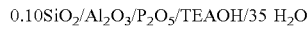

$0.10 SiO_2/Al_2O_3/P_2O_5/TEAOH/35 H_2O$

The autoclave was heated at 20° C./hour to 150° C. and then maintained at this temperature for 112 hours, with the mixture being stirred with a laboratory mixer at 600 rpm (tip speed of 3.1 m/s) during the whole hydrothermal treatment. After cooling to room temperature, a sample of the slurry was washed and dried and an X-ray diffraction pattern of the crystalline product was taken and was identified as AlPO—C, a partial dehydrated form of AlPO—H3.

The rest of the synthesis mixture was stored for 20 days at room temperature without agitation. After the storage, part of the slurry was transferred to a 300 ml stainless steel autoclave and re-heated, without agitation, in 8 hrs to 175° C. and then maintained at this temperature for 48 hrs. After cooling the slurry was washed and dried and a sample was taken for calcination and XRD analysis. The DIFFaX ratio of the sample was 20/80. The yield of the dried product was 21.3 wt % and the Si/Al2 was 0.15.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

I claim:

1. A method of synthesizing a silicoaluminophosphate molecular sieve comprising at least one intergrown phase of an AEI framework type material and a CHA framework type material, the method comprising:
   (a) preparing a first synthesis mixture comprising water and sources of phosphorus, aluminum and optionally silicon;
   (b) heating said first synthesis mixture under agitation to a first temperature of from about 99° C. to about 150° C. to form an intermediate product mixture containing a silicoaluminophosphate or aluminophosphate precursor material; and
   (c) cooling and storing the intermediate product mixture at a second temperature less than 50° C.;
   (d) preparing a second synthesis mixture comprising at least part of said intermediate product mixture from (c) and at least one organic directing agent and, if necessary, a silicon source to provide a $SiO_2:Al_2O_3$ ratio within said second synthesis mixture of from about 0.05 to about 0.3;
   (e) heating said second synthesis mixture, under static conditions or with reduced agitation in comparison with that used during heating of said first synthesis mixture, to a third temperature higher than said first temperature and from about 150° C. to about 220° C. to convert at least part of said precursor material into said molecular sieve; and
   (f) recovering said molecular sieve.

2. The method of claim 1, wherein the first temperature is about 115° C. to about 125° C.

3. The method of claim 1, wherein the second temperature is about 0° C. to about 30° C.

4. The method of claim 1, wherein the third temperature is about 165° C. to about 190° C.

5. The method of claim 1, wherein the pH of the first synthesis mixture is less than 2.

6. The method of claim 1, wherein the pH of the first synthesis mixture is between about 1.1 and about 1.5.

7. The method claim 1, wherein the $P_2O_5:Al_2O_3$ of the first synthesis mixture is between about 0.7 and about 1.0.

8. The method of claim 1, wherein the $P_2O_5:Al_2O_3$ of the first synthesis mixture is between about 0.75 and about 0.9.

9. The method of claim 1, wherein the first synthesis mixture comprises said at least one organic directing agent.

10. The method of claim 9, wherein the second synthesis mixture has the same composition as the intermediate product mixture.

11. The method of claim 1, wherein the molar ratio of organic directing agent (R) to $Al_2O_3$ in the second synthesis mixture is greater than that of the first synthesis mixture.

12. The method of claim 11, wherein the $R:Al_2O_3$ molar ratio of the second synthesis mixture is greater than 0.6.

13. The method of claim 11, wherein the $R:Al_2O_3$ molar ratio of the second synthesis mixture is about 0.65 to about 1.

14. The method of claim 11, wherein the $R:Al_2O_3$ molar ratio of the first synthesis mixture is less than 0.7.

15. The method of claim 11, wherein the $R:Al_2O_3$ molar ratio of the first synthesis mixture is about 0.2 to about 0.6.

16. The method of claim 1, wherein the $H_2O:Al_2O_3$ molar ratio of the first synthesis mixture is at least 30.

17. The method of claim 1, wherein the $H_2O:Al_2O_3$ molar ratio of the first synthesis mixture is about 30 to about 50.

18. The method of claim 1, wherein said precursor material comprises at least one of ALPO-H3, variscite and metavariscite.

19. The method of claim 1 and also comprising reducing the water content of the intermediate product mixture prior to storage thereof.

20. The method of claim 19, wherein preparing the second synthesis mixture in (d) also comprises adding water to said intermediate product mixture from (c).

21. The method of claim 1, wherein the $H_2O:Al_2O_3$ molar ratio of the second synthesis mixture is the same as that of the first synthesis mixture.

22. The method of claim 1, wherein the heating in (b) is conducted so as to raise the temperature of said first synthesis mixture at a rate of at least 8° C./hour.

23. The method of claim 1, wherein the heating in (b) is conducted so as to raise the temperature of said first synthesis mixture at a rate of from about 10° C./hour to about 40° C./hour.

24. The method of claim 1, wherein the heating (e) is conducted without agitation.

25. The method of claim 1, wherein the heating in (e) is conducted so as to raise the temperature of said first synthesis mixture at a rate of at least 8° C./hour.

26. The method of claim 1, wherein the heating in (e) is conducted so as to raise the temperature of said first synthesis mixture at a rate of from about 10° C./hour to about 40° C./hour.

27. The method of claim 1, wherein (c) comprises storing said cooled intermediate product mixture for at least 2 hours before the heating (e).

28. The method of claim 1, wherein (c) comprises storing said cooled intermediate product mixture for about 30 hours to about 30 days before the heating (e).

29. The method of claim 1, wherein said at least one intergrown phase has an AEI/CHA ratio of from about 5/95 to about 40/60 as determined by DIFFaX analysis.

30. The method of claim 1, wherein said at least one intergrown phase has an AEI/CHA ratio of from about 10/90 to about 30/70 as determined by DIFFaX.

31. The method of claim 1, wherein said at least one intergrown phase has an AEI/CHA ratio of from about 15/95 to about 20/80 as determined by DIFFaX.

32. The method of claim 29, wherein said silicoaluminophosphate molecular sieve has an X-ray diffraction pattern comprising at least one reflection peak in each of the following ranges in the 5 to 25 (2θ) range:

| 2θ (CuKα) |
| --- |
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0. |

33. The method of claim 1, wherein said silicoaluminophosphate molecular sieve comprises first and second intergrown phases each of an AEI framework type material and a CHA framework type material.

34. The method of claim 33, wherein said first intergrown phase has an AEI/CHA ratio of from about 5/95 to about 40/60 as determined by DIFFaX analysis and said second intergrown phase has a different AEI/CHA ratio from said first intergrown form.

35. The method of claim 34, wherein said second intergrown phase has an AEI/CHA ratio of about 30/70 to about 55/45 as determined by DIFFaX analysis.

36. The method of claim 34, wherein said second intergrown phase has an AEI/CHA ratio of about 50/50 as determined by DIFFaX analysis.

* * * * *